United States Patent
Kawamura et al.

(10) Patent No.: US 10,654,793 B2
(45) Date of Patent: May 19, 2020

(54) PRODUCTION METHOD FOR 1-AMINO CYCLOPROPANE CARBOXYLIC ACID NONHYDRATE

(71) Applicant: SUMITOMO CHEMICAL COMPANY, LIMITED, Tokyo (JP)

(72) Inventors: Mitsunobu Kawamura, Osaka (JP); Hiroaki Okamoto, Oita (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/611,577

(22) PCT Filed: May 2, 2018

(86) PCT No.: PCT/JP2018/017481
§ 371 (c)(1),
(2) Date: Nov. 7, 2019

(87) PCT Pub. No.: WO2018/207693
PCT Pub. Date: Nov. 15, 2018

(65) Prior Publication Data
US 2020/0095188 A1    Mar. 26, 2020

(30) Foreign Application Priority Data
May 8, 2017 (JP) ................. 2017-092614

(51) Int. Cl.
C07C 227/16  (2006.01)
C07C 229/46  (2006.01)

(52) U.S. Cl.
CPC ......... *C07C 227/16* (2013.01); *C07C 229/46* (2013.01)

(58) Field of Classification Search
CPC ............... C07C 227/16; C07C 229/46
USPC ......................................... 562/506
See application file for complete search history.

(56) References Cited

U.S. PATENT DOCUMENTS 4,367,344 A * 1/1983 Gallenkamp .......... A01N 53/00
                                                         504/171

FOREIGN PATENT DOCUMENTS

JP    41-16862 B1    9/1966
JP    56-45443 A     4/1981

OTHER PUBLICATIONS

International Search Report, issued in PCT/JP2018/017481, PCT/ISA/210, dated Jul. 17, 2018.
Salaun et al., "A New and Convenient Preparation of 1-Aminocyclopropanecarboxylic Acid from Acrolein", J. Org. Chem., 1990, vol. 55, pp. 4276-4281.

* cited by examiner

*Primary Examiner* — Yong L Chu
(74) *Attorney, Agent, or Firm* — Birch, Stewart, Kolasch & Birch, LLP

(57) ABSTRACT

1-Aminocyclopropanecarboxylic acid non-hydrate can be obtained by
treating 1-aminocyclopropanecarboxylic acid hydrochloride with a tertiary amine in the presence of a $C_3$-$C_4$ alcohol and water,
keeping the reaction mixture at 50° C. or below,
collecting the precipitated crystal of 1-aminocyclopropanecarboxylic acid 0.5 hydrate by filtration, and
heating the obtained crystal to 80 to 245° C.

5 Claims, 2 Drawing Sheets

PRODUCTION METHOD FOR 1-AMINO CYCLOPROPANE CARBOXYLIC ACID NONHYDRATE

TECHNICAL FIELD

The present invention relates to production of 1-aminocyclopropanecarboxylic acid non-hydrate.

BACKGROUND ART

1-Aminocyclopropanecarboxylic acid is known as a plant growth regulator.

A production method of 1-aminocyclopropanecarboxylic acid hydrochloride is known in Patent Document 1 and Non-Patent Document 1. A method of converting 1-aminocyclopropanecarboxylic acid hydrochloride into a free form of 1-aminocyclopropanecarboxylic acid is also described in Patent Document 1 and Non-Patent Document 1. However, the method is hardly suitable for industrial production.

DOCUMENT LIST

Patent Document

Patent Document 1: U.S. Pat. No. 4,367,344

Non-Patent Document

Non-Patent Document 1: Journal of Organic Chemistry (J. Org. Chem.) 1990, vol. 55, pages 4276-4281

SUMMARY OF THE INVENTION

The present invention provides a production method of 1-aminocyclopropanecarboxylic acid non-hydrate.

Treating 1-aminocyclopropanecarboxylic acid hydrochloride with a tertiary amine in the presence of a $C_3$-$C_4$ alcohol and water facilitates the crystallization of a free form of 1-aminocyclopropanecarboxylic acid 0.5 hydrate, while preventing the crystallization of the tertiary amine hydrochloride. In the present invention, first, the 0.5 hydrate superior in filtration property is obtained, and then is heated to 80 to 245° C. to obtain 1-aminocyclopropanecarboxylic acid non-hydrate.

Accordingly, the present invention provides the following.

[1] A method of producing 1-aminocyclopropanecarboxylic acid non-hydrate, which comprises
treating 1-aminocyclopropanecarboxylic acid hydrochloride with a tertiary amine in the presence of a $C_3$-$C_4$ alcohol and water,
keeping the reaction mixture at 50° C. or below,
collecting the precipitated crystal of 1-aminocyclopropanecarboxylic acid 0.5 hydrate by filtration, and
heating the obtained crystal to 80 to 245° C.
[2] The method of the above-mentioned [1], wherein the tertiary amine is triethylamine.
[3] The method of the above-mentioned [1] or [2], wherein the temperature for heating the crystal of 1-aminocyclopropanecarboxylic acid 0.5 hydrate is 80 to 150° C.
[4] The method of any of the above-mentioned [1] to [3], wherein the $C_3$-$C_4$ alcohol is 2-propanol.
[5] The method of any of the above-mentioned [1] to [4], which further comprises a step of subjecting a $C_1$-$C_4$ alkyl 1-acetylaminocyclopropanecarboxylate to hydrolysis using hydrochloric acid to obtain 1-aminocyclopropanecarboxylic acid hydrochloride.

According to the present invention, since a free form of 1-aminocyclopropanecarboxylic acid 0.5 hydrate, which is obtained from 1-aminocyclopropanecarboxylic acid hydrochloride, can be easily crystallized, it can be obtained in good yield in simple process. In addition, the 0.5 hydrate can be easily converted into the non-hydrate by heating. The production method of the present invention can provide a free form of 1-aminocyclopropanecarboxylic acid non-hydrate with a high purity in simple process, and therefore, it is suitable for industrial production.

DESCRIPTION OF EMBODIMENTS

Figure 1:
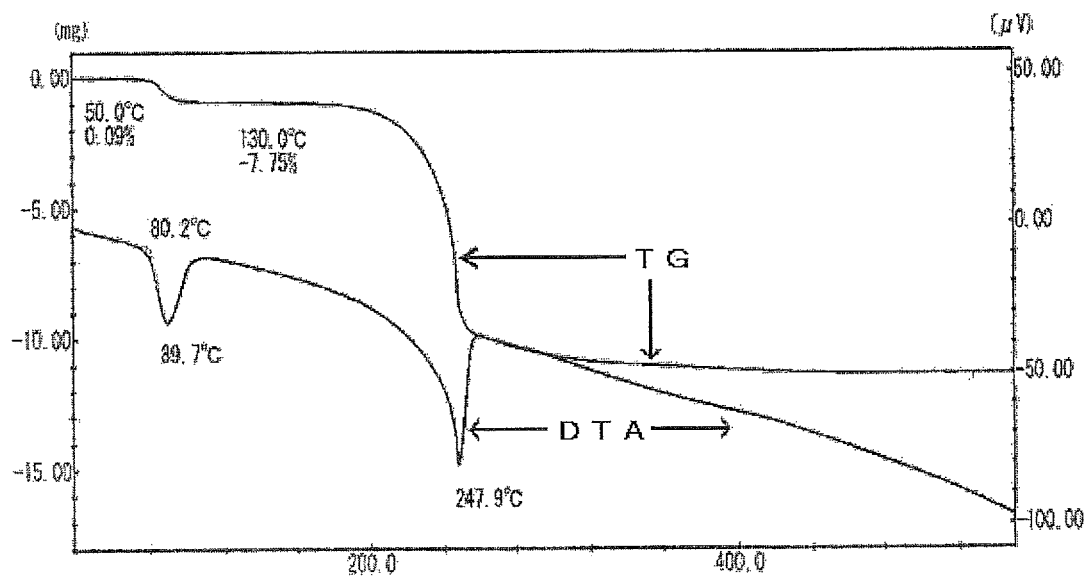
FIG. 1 shows measurement results of thermogravimeter-differential thermal analysis (TG-DTA) of 1-aminocyclopropanecarboxylic acid 0.5 hydrate.

The present invention is explained in detail below.

1-Aminocyclopropanecarboxylic acid hydrochloride can be obtained by subjecting 1-aminocyclopropanecarbonitrile to hydrolysis using hydrochloric acid, according to the description of Non-Patent Document 1. In addition, the compound can also obtained by subjecting ethyl 1-acetylaminocyclopropanecarboxylate to hydrolysis using hydrochloric acid, according to the description of Patent Document 1.

In the present invention, the treatment step with a tertiary amine is carried out advantageously on the 1-aminocyclopropanecarboxylic acid hydrochloride obtained by subjecting a $C_1$-$C_4$ alkyl 1-acetylaminocyclopropanecarboxylate to hydrolysis using hydrochloric acid.

The $C_1$-$C_4$ alkyl 1-acetylaminocyclopropanecarboxylate can be produced according to the description in Patent Document 1. The hydrolysis reaction is carried out according to a method known per se, for example by adding hydrochloric acid to a mixture of the $C_1$-$C_4$ alkyl 1-acetylaminocyclopropanecarboxylate and water, and then heating the mixture. The concentration of the hydrochloric acid is generally 1 to 25%, the reaction temperature is generally 70 to 110° C., and the reaction time is generally 0.5 to 24 hr. The amount of the hydrochloric acid to be used is generally 1.0 to 3.0 mol, preferably 1.5 to 2.0 mol, as a HCl amount, per 1 mol of the $C_1$-$C_4$ alkyl 1-acetylaminocyclopropanecarboxylate. The hydrolysis reaction may be carried out while evaporating acetic acid and methanol generated during the reaction, and methyl acetate generated by condensation of the acetic acid and methanol.

Thus obtained hydrochloric acid solution containing 1-aminocyclopropanecarboxylic acid hydrochloride may be directly used in the next treatment step with a tertiary amine, without isolation.

Examples of the $C_1$-$C_4$ alkyl ester include methyl ester, ethyl ester, 1-propyl ester, 2-propyl ester, 1-butyl ester, tert-butyl ester and the like, preferred are $C_1$-$C_2$ alkyl esters, and particularly preferred is a $C_1$ alkyl ester, i.e., methyl ester.

The step of treating 1-aminocyclopropanecarboxylic acid hydrochloride with a tertiary amine is explained below.

The term "$C_3$-$C_4$ alcohol" herein means an alcohol having 3 to 4 carbon atoms, and examples thereof include 1-propanol, 2-propanol, 1-butanol, 2-methylpropan-1-ol, 2-butanol and 2-methyl-2-propanol. Among them, preferred is 2-propanol in terms of crystallization efficiency of 1-aminocyclopropanecarboxylic acid 0.5 hydrate, miscibility with water, and solubility of the tertiary amine hydrochloride.

The amount of the $C_3$-$C_4$ alcohol to be used is generally 1 to 10 parts by weight, preferably 1 to 3 parts by weight from industrial aspect, per 1 part by weight of the 1-aminocyclopropanecarboxylic acid hydrochloride.

The amount of the water to be used is generally 1 to 10 parts by weight, preferably 1 to 3 parts by weight from industrial aspect, per 1 part by weight of the 1-aminocyclopropanecarboxylic acid hydrochloride. In addition, the amount is generally 0.5 to 2 parts by weight, per 1 part by weight of the $C_3$-$C_4$ alcohol, and the amount is determined so that the generated tertiary amine hydrochloride can be dissolved, depending on the kind of the alcohol, and the mixing ratio with the alcohol.

Examples of the tertiary amine include trimethylamine, triethylamine, N,N-diisopropylethylamine and the like. Among them, preferred is triethylamine in terms of easy handling, and high solubility of the generated tertiary amine hydrochloride in the mixture of a $C_3$-$C_4$ alcohol and water.

The amount of the tertiary amine to be used is an amount sufficient to adjust the pH of the reaction system to 5.0 to 7.0, preferably 5.5 to 6.5.

The treatment with a tertiary amine is generally carried out by mixing 1-aminocyclopropanecarboxylic acid hydrochloride, a $C_3$-$C_4$ alcohol, water and a tertiary amine. Specifically, (1) a method of adding a tertiary amine to a mixture of 1-aminocyclopropanecarboxylic acid hydrochloride and a $C_3$-$C_4$ alcohol and water, (2) a method of adding 1-aminocyclopropanecarboxylic acid hydrochloride (plus water if necessary) to a mixture of a $C_3$-$C_4$ alcohol and a tertiary amine (plus water if necessary), and (3) a method of adding a $C_3$-$C_4$ alcohol to a mixture of 1-aminocyclopropanecarboxylic acid hydrochloride, a tertiary amine and water, are exemplified. Among them, preferred are the methods of (1) and (2) in terms of purity of the obtained crystals. The addition may be dropwise addition. The addition is generally carried out at 10 to 100° C., preferably at 20 to 30° C.

After the treatment with a tertiary amine, by keeping the reaction mixture at 50° C. or below, generally at 40° C. or below, preferably at 10 to 40° C., more preferably at 20 to 30° C., preferably under stirring, 1-aminocyclopropanecarboxylic acid 0.5 hydrate is crystallized. The stirring is generally carried out for 1 to 24 hr, preferably 2 to 15 hr.

The 0.5 hydrate is a stable and block-like crystal superior in filtration property relative to the non-hydrate being a micaceous crystal. Hence, with the 0.5 hydrate, the filtration step and washing step can be advantageously carried out in a short time, leaving much less amount of the tertiary amine.

The crystallization of the 0.5 hydrate can be facilitated by using seed crystals of the 0.5 hydrate.

The precipitated crystals are collected by filtration to obtain 1-aminocyclopropanecarboxylic acid 0.5 hydrate.

The thermogravimeter-differential thermal analysis (TG-DTA) of 1-aminocyclopropanecarboxylic acid 0.5 hydrate was measured under the following conditions. FIG. 1 shows the results of the analysis.

Measurement of thermogravimeter-differential thermal analysis (TG-DTA)

1-Aminocyclopropanecarboxylic acid 0.5 hydrate (about 15 mg) was put into a pan made of aluminium, and TG-DTA measurement was performed using thermogravimeter-differential thermal analyzer TG-DTA2000SR (Bruker) under the following conditions.

pan: cylindrical sample cup (φ5.2 mm) made of aluminium (Netzsch Japan J1560180)
sample amount: about 15 mg
measurement temperature: 30° C.-550° C.
raising rate: 5° C./min
atmosphere: $N_2$ 150 mL/min As is clear from FIG. 1, the transition from 1-aminocyclopropanecarboxylic acid 0.5 hydrate to the non-hydrate starts at about 80° C. Therefore, by heating the obtained 1-aminocyclopropanecarboxylic acid 0.5 hydrate to 80° C. or above, generally 80 to 245° C., preferably 80 to 150° C., the 0.5 hydrate can be converted into the non-hydrate. The obtained non-hydrate may be dried under reduced pressure, if necessary. The drying time is generally 30 min to 40 hr, preferably 30 min to 25 hr.

EXAMPLES

The present invention is concretely explained by referring to the following Examples and Reference Example.

The average specific filtration resistance was measured by the following method.

Measurement of Average Specific Filtration Resistance

The filtration rate was measured by the following method to calculate the average specific filtration resistance.

The slurry liquid was put into a pressure-resistant container, and the container was sealed, and pressurized to a predetermined pressure. The bottom valve was opened to start the filtration. The filtrate weight was measured every predetermined time to calculate the filtration rate, until the filtration was completed, and then the container was depressurized. The container was opened, and the wet cake thickness was measured. The wet cake was taken out, weighed, and dried under reduced pressure at 85° C., and the liquid content was calculated.

The average specific filtration resistance value was calculated according to the following formula using the data of filtration rate, filtration area, filtrate viscosity, wet cake weight, liquid content, wet cake thickness and filtration pressure.

$$\frac{\theta}{V} = \frac{V}{K} + \frac{2V_0}{K}$$

$K = 2 \cdot \Delta P \cdot A^2 \cdot gc/(\mu \cdot \alpha m \cdot C)$
$V_0 = Rm \cdot A/(\alpha m \cdot C)$
θ: filtration time
V: filtrate volume
θ/V: reciprocal of filtration rate
μ: filtrate viscosity
ΔP: pressure difference (=filtration pressure)
A: filtration area
gc: gravitational acceleration
αm: average specific filtration resistance
C: solid concentration
Rm: filter cloth resistance The measurement conditions for X-RAY diffraction (XRD) are as follows.
measurement conditions for X-RAY diffraction (XRD)
X-RAY diffraction apparatus: SmartLab (Rigaku)

X-RAY output: CuKα, 45 kV, 200 mA
sampling width: 0.02°
scanning field: 5°-50°

The water content was measured by Karl Fischer method using coulometric Karl Fischer moisture analyzer (CA-200, Mitsubishi Chemical Analytech).

Example 1

To 1-aminocyclopropanecarboxylic acid hydrochloride (purity 98.7%, 2 g) were added water (2.7 g) and 2-methylpropan-1-ol (4.6 g). Triethylamine (1.5 g) was added thereto to adjust the pH to 6.0, the obtained slurry was cooled to 20° C., and the precipitated crystals were collected by filtration. The obtained crystals were washed with 2-methylpropan-1-ol (10.6 g), and dried under reduced pressure at 85° C. for 3 hr to give 1-aminocyclopropanecarboxylic acid non-hydrate (1.2 g, content: 99.5% (yield 84.1%), water content: 0.26%).

Example 2

Figure 2:
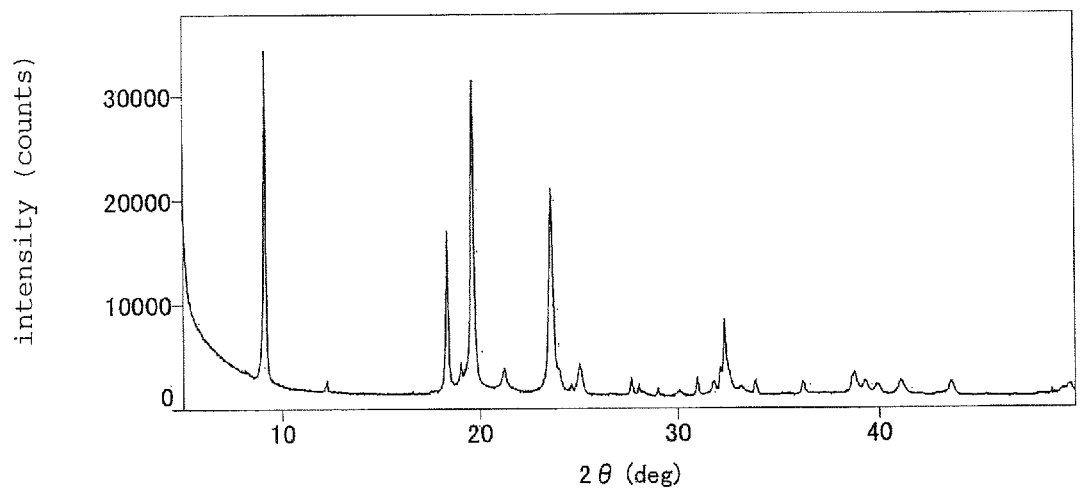
FIG. 2 shows X-RAY diffraction (XRD) measurement results of 1-aminocyclopropanecarboxylic acid non-hydrate.

To a mixture of 1-aminocyclopropanecarboxylic acid hydrochloride (purity 84.7%, 2 g) and 10% hydrochloric acid (4.0 g) was added 2-propanol (5.5 g). To the obtained solution was added triethylamine (2.7 g) to adjust the pH to 5.6, the obtained slurry was cooled to 15° C., and the precipitated crystals were collected by filtration. The obtained wet crystals were washed with 2-propanol (1.7 g), and dried under reduced pressure at 80° C. for 3 hr to give 1-aminocyclopropanecarboxylic acid non-hydrate (1.1 g, content: 99.7% (yield 91.1%), water content: 0.18%). FIG. 2 shows the X-RAY diffraction (XRD) measurement results of the obtained 1-aminocyclopropanecarboxylic acid non-hydrate.

Reference Example 3

Figure 3:
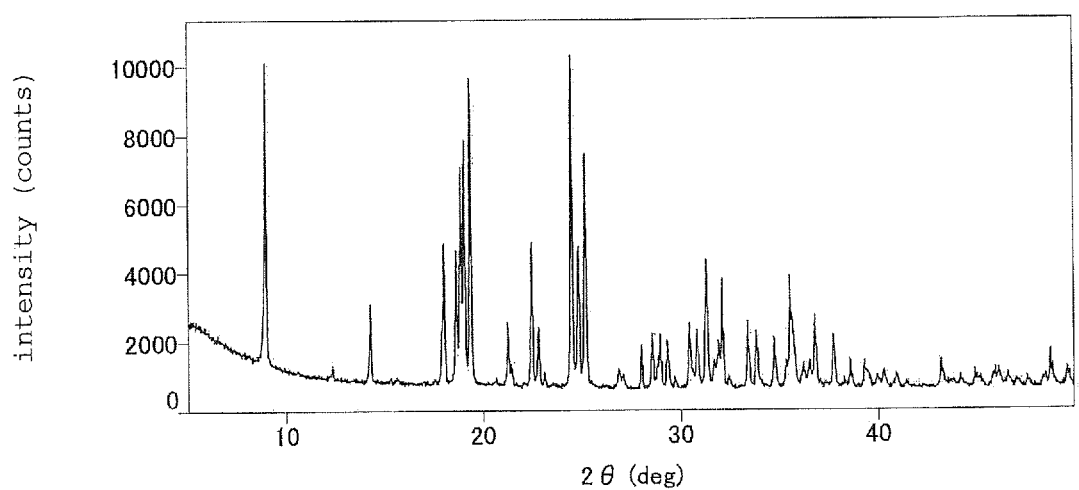
FIG. 3 shows X-RAY diffraction (XRD) measurement results of 1-aminocyclopropanecarboxylic acid 0.5 hydrate.

To a mixture of 1-aminocyclopropanecarboxylic acid hydrochloride (purity: 84.7%, 10 g) and 10% hydrochloric acid (4.0 g) was added 1-butanol (16.8 g). To the obtained solution was added triethylamine (13.2 g) to adjust the pH to 5.6, the obtained slurry was cooled to 16° C., and the precipitated crystals were collected by filtration. The obtained wet crystals were washed with 1-butanol (8.3 g), and dried under reduced pressure at 50° C. for 3 hr to give 1-aminocyclopropanecarboxylic acid 0.5 hydrate (5.83 g, content: 92.0% (yield 86.2%), water content: 8.0%). FIG. 3 shows the X-RAY diffraction (XRD) measurement results of the obtained 1-aminocyclopropanecarboxylic acid 0.5 hydrate.

Example 4

To a solution (73.6 g, content 24.0%) prepared by dissolving 1-aminocyclopropanecarboxylic acid hydrochloride in 10% hydrochloric acid was added water (3.5 g), and then 2-propanol (53.6 g) was added thereto at 20° C. The obtained solution was warmed to 25° C., and triethylamine (29.7 g) was added dropwise thereto over 5 hr. Immediately after the completion of the addition, a part of the precipitated crystals was separately collected by filtration. The reading of the water content measurement of the crystal was 8.2%, based on which the crystal was confirmed to be 0.5 hydrate. The average specific filtration resistance was 5×10$^8$ m/kg when the remaining part of the crystals was filtered. The obtained wet crystals were washed with 2-propanol (26.9 g). The crystals are dried under reduced pressure at 85° C. for 25 hr to give 1-aminocyclopropanecarboxylic acid non-hydrate.

Example 5

To methyl 1-acetylaminocyclopropanecarboxylate (purity, 65%, 39.9 g) was added water (12.6 g), and the mixture was heated to 100° C. 35% Hydrochloric acid (28.3 g) was added dropwise thereto over 5 hr, and the mixture was kept at the same temperature for 10 hr to give a hydrochloric acid solution containing 1-aminocyclopropanecarboxylic acid hydrochloride (22.4 g, yield 98.4%).

To the obtained hydrochloric acid solution containing the crude 1-aminocyclopropanecarboxylic acid hydrochloride was added water (19.1 g), and the mixture was added dropwise to a mixture of 2-propanol (51.9 g), triethylamine (28.4 g), water (3.3 g) and 1-aminocyclopropanecarboxylic acid 0.5 hydrate (50 mg) over 5 hr at 25° C. After the completion of the addition, triethylamine was added thereto to adjust the pH to 6.0, and the mixture was stirred at 25° C. for 12 hr. A part of the precipitated crystals was separately collected by filtration. The crystal was confirmed to be 0.5 hydrate based on the water content measurement of the crystal. The remaining part of the crystals was collected by filtration, and the obtained wet crystals were washed with 2-propanol (26.0 g). The crystals are dried under reduced pressure at 85° C. for 25 hr to give 1-aminocyclopropanecarboxylic acid non-hydrate.

Example 6

To a solution (55.0 g, content 22.1%) prepared by dissolving 1-aminocyclopropanecarboxylic acid hydrochloride in 10% hydrochloric acid was added dropwise triethylamine (21.7 g) over 5 hr at 60° C., and then 2-propanol (40 g) was added dropwise thereto over 5 hr. Then, triethylamine (1.7 g) was added thereto to adjust the pH to 6.0, and the mixture was cooled to 25° C. over 7 hr. A part of the precipitated crystals was separately collected by filtration. The reading of the water content measurement of the crystal was 1.2%, based on which 85% or more of the crystal was confirmed to be non-hydrate. The average specific filtration resistance was 2×10$^{10}$ m/kg when the remaining part of the crystals was filtered. The obtained wet crystals were washed with 2-propanol (20.2 g). The crystals are dried under reduced pressure at 85° C. for 25 hr to give 1-aminocyclopropanecarboxylic acid non-hydrate.

Example 7

A solution (70.6 g, content 22.1%) prepared by dissolving 1-aminocyclopropanecarboxylic acid hydrochloride in 10% hydrochloric acid was added dropwise to a mixture of triethylamine (23.5 g), 2-propanol (42.9 g), water (2.7 g) and 1-aminocyclopropanecarboxylic acid 0.5 hydrate (50 mg) over 5 hr at 20° C. A part of the precipitated crystals was separately collected by filtration. The reading of the water content measurement of the crystal was 8.4%, based on which the crystal was confirmed to be 0.5 hydrate. The average specific filtration resistance was 8×10$^8$ m/kg when the remaining part of the crystals was filtered.

INDUSTRIAL APPLICABILITY

According to the present invention, 1-aminocyclopropanecarboxylic acid 0.5 hydrate can be obtained in simple process from 1-aminocyclopropanecarboxylic acid hydrochloride. Moreover, 1-aminocyclopropanecarboxylic acid non-hydrate being a plant growth regulator can be easily obtained by heating the 0.5 hydrate to 80 to 245° C.

The invention claimed is:

1. A method of producing 1-aminocyclopropanecarboxylic acid non-hydrate, which comprises treating 1-aminocyclopropanecarboxylic acid hydrochloride with a tertiary amine in the presence of a $C_3$-$C_4$ alcohol and water, keeping the reaction mixture at 50° C. or below, collecting the precipitated crystal of 1-aminocyclopropanecarboxylic acid 0.5 hydrate by filtration, and heating the obtained crystal to 80 to 245° C.

2. The method according to claim 1, wherein the tertiary amine is triethylamine.

3. The method according to claim 1, wherein the temperature for heating the crystal of 1-aminocyclopropanecarboxylic acid 0.5 hydrate is 80 to 150° C.

4. The method according to claim 1, wherein the $C_3$-$C_4$ alcohol is 2-propanol.

5. The method according to claim 1, which further comprises a step of subjecting a $C_1$-$C_4$ alkyl 1-acetylaminocyclopropanecarboxylate to hydrolysis using hydrochloric acid to obtain 1-aminocyclopropanecarboxylic acid hydrochloride.

* * * * *